(12) United States Patent
Weinkauff et al.

(10) Patent No.: US 6,399,814 B1
(45) Date of Patent: Jun. 4, 2002

(54) PROCESS FOR THE PREPARATION OF 2-CARBOXYALKYL(ARYL)PHOSPHINIC ACID AND CORRESPONDING ANHYDRIDE(S)

(75) Inventors: David J. Weinkauff, Manchester; Frank E. Paulik, St. Louis, both of MO (US)

(73) Assignee: Solutia Inc., St. Louis, MO (US)

( * ) Notice: Subject to any disclaimer, the term of this patent is extended or adjusted under 35 U.S.C. 154(b) by 0 days.

(21) Appl. No.: 09/528,954

(22) Filed: Mar. 20, 2000

(51) Int. Cl.[7] .................................................. C07C 9/30
(52) U.S. Cl. ........................................... 562/24; 562/23
(58) Field of Search ....................................... 562/24, 23

(56) References Cited

U.S. PATENT DOCUMENTS

| | | | |
|---|---|---|---|
| 4,081,463 A | 3/1978 | Birum et al. ......... | 260/502.4 R |
| 4,769,182 A | 9/1988 | Hazen ................. | 260/502.4 R |
| 5,334,760 A | 8/1994 | Wachi et al. ............... | 562/817 |
| 6,090,976 A | * 7/2000 | Kim et al. .................... | 562/24 |

* cited by examiner

Primary Examiner—Jean F. Vollano
(74) Attorney, Agent, or Firm—Lathrop & Gage LC

(57) ABSTRACT

An improved hydrolysis process comprising a process for the preparation of 2-carboxyalkyl(aryl)phosphinic acid using a controlled addition of water to an acrylation reaction mixture, and control of the temperature. Preparation of 2-carboxyalkyl(aryl)phosphinic acid cyclic anhydride is disclosed using a controlled addition of water, wherein up to about one mole of water per mole of dichloro(aryl)phosphine charged to the acrylation reaction is added, and temperature is controlled.

15 Claims, 7 Drawing Sheets

US 6,399,814 B1

PROCESS FOR THE PREPARATION OF 2-CARBOXYALKYL(ARYL)PHOSPHINIC ACID AND CORRESPONDING ANHYDRIDE(S)

FIELD OF THE INVENTION

This invention relates to a process for preparing 2-carboxyalkyl(aryl)phosphinic acid and its corresponding anhydride(s). More specifically, this invention relates to a process for preparing 2-carboxyethyl(aryl)phosphinic acid using an improved hydrolysis process for intermediates involved in the overall reaction. In particular, this invention relates to a process for preparing 2-carboxyethyl(phenyl) phosphinic acid and its cyclic anhydride.

BACKGROUND OF THE INVENTION

2-Carboxyethyl(phenyl)phosphinic acid, useful as a flame retardant additive for polymers such as polyesters and polyamides, has been prepared by reacting acrylic acid with dichloro(phenyl)phosphine in a reaction mixture. This reaction mixture was subjected to a separate hydrolysis step to obtain the desired product: 2-carboxyethyl(phenyl) phosphinic acid.

2-Carboxyethyl(aryl)phosphinic acid and its cyclic anhydride are useful as flame retardant additives for polymers such as polyesters, polyamides and the like.

U.S. Pat. No. 5,334,760 which issued on Aug. 2, 1994, to Toshio Wachi et al. (hereinafter "the '760 patent") discloses a process in which acrylic acid or methacrylic acid is reacted with dichloro(phenyl)phosphine in the presence of a catalyst (Column 1, lines 51–68). That reaction product is hydrolyzed as the '760 patent subsequently discloses:

With the reaction product wherein water is added at a molar amount of 5 to 20 times of the reaction product or with the reaction product dropped in water having the same molar amount as the above, a reaction is carried out at a temperature of 0° to 100° C. for 1 to 3 hours. After completion of the reaction, the resulting reaction product is cooled under stirring, so that a crystal is deposited. (Column 4, line 62-Column 5, line 1).

The '760 patent is incorporated herein in its entirety by reference.

U.S. Pat. No. 4,081,463 which issued to Birum et al. on Mar. 28, 1978 (hereinafter the "463 patent") discloses, at column 1, lines 21–25, a process in which a 25–45% molar excess of acrylic acid was used in a reaction of acrylic acid with dichloro(phenyl)phosphine. The '463 patent is incorporated herein in its entirety by reference. For the hydrolysis step, the '463 patent discloses adding the undiluted reaction product of acrylic acid and dichloro(phenyl)phosphine to at least enough water to complete hydrolysis, with it being reportedly advantageous to use a significant excess of water to aid stirring and temperature control. Use of a 5 to 15 molar excess of water is taught at column 1, lines 58–60, as being convenient. This molar excess of water is equivalent to conducting the hydrolysis reported in this patent using 12 to 32 moles water per mole of dichloro(phenyl)phosphine charged to the reaction of acrylic acid with dichloro(phenyl) phosphine.

U.S. Pat. No. 4,769,182 which issued to James R. Hazen on Sep. 6, 1988, (hereinafter the "'182 patent") discloses at column 2, lines 30–38, a process in which a 0–20% molar excess of acrylic acid was used in the reaction of acrylic acid with dichloro(phenyl)phosphine. The '182 patent is incorporated herein by reference in its entirety. In its hydrolysis step, the '182 patent discloses that typical hydrolysis conditions for acid chlorides and similar water-reactive species are used, with a "drowning" technique being preferred, see column 4 lines 45–48. This "drowning" technique involves the use of significant excess water, i.e. 25.7 moles water per mole of dichloro(phenyl)phosphine charged to the reaction of acrylic acid with dichloro(phenyl)phosphine. Conducting the hydrolysis in this manner reportedly produces 2-carboxyethyl(phenyl)phosphinic acid as a white microcrystalline powder. However, by avoiding a solid phase and driving off hydrogen halides (e.g. HCl) to improve crystal size, the instant invention produces a purer product with less net trapped impurities.

It is desirable to produce 2-carboxyalkyl(aryl)phosphinic acid with improved product recovery and washing, resulting in improved product quality. This improved quality provides a 2-carboxyalkyl(aryl)phosphinic acid product for use in a polymerization process producing a flame retardant polymer with better color quality, lower catalyst losses in such process, and less corrosion of processing and handling equipment.

It has now been discovered that conducting the hydrolysis with significantly less water present than taught or suggested by the prior art produces 2-carboxyalkyl(aryl)phosphinic acid having enhanced filterability, washing and flowability properties along with a higher bulk density. Enhanced filterability lowers process cycle times and increases productivity.

It has been unexpectedly discovered that the controlled water addition of the process of this invention to the reaction composition avoids a premature solid phase.

Further, it has been discovered herein that by adding water to the reaction composition according to the process of the instant invention, that hydrogen halide (e.g. HCl) is given off in larger than expected quantities, allowing for the formation of larger, more durable crystal size, which improves the resultant product purity, washing, drying, and filterability.

OBJECTS OF THE INVENTION

It is an object of the invention to provide a process for producing 2-carboxyalkyl(aryl)phosphinic acid having improved filterability.

It is a further object of this invention to provide a process to produce 2-carboxyalkyl(aryl)phosphinic acid having lower levels of impurities.

It is a still further object of the invention to provide a process for producing 2-carboxyalkyl(aryl)phosphinic acid which results in improved product washing, faster filtration and better flowability of the final product, each of which can aid in facilitating and enhancing packaging of 2-carboxyalkyl(aryl)phosphinic acid of this invention.

It is yet a further object of the invention to provide a process for producing 2-carboxyalkyl(aryl)phosphinic acid which enables hydrogen halide produced (e.g. HCl) during the hydrolysis reaction to be removed prior to recovery of 2-carboxyalkyl(aryl)phosphinic acid from the hydrolysis reaction mixture, thereby lowering the level of halide in the final product and enhancing 2-carboxyalkyl(aryl)phosphinic acid crystal size (lower levels of halide minimizes corrosion of metal equipment in uses of 2-carboxyalkyl(aryl) phosphinic acid such as in polymer applications).

It is another object of this invention to avoid an unstirrable or difficult to stir solid in a reaction producing 2-carboxyalkyl(aryl)phosphinic acid for an easier and safer process.

It is an additional object of this invention to provide a process to produce an anhydride corresponding to 2-carboxyalkyl(aryl)phosphinic acid.

These and other objects are achieved in the process of this invention which is described in more non-limiting detail hereinafter.

BRIEF SUMMARY OF THE INVENTION

The invention comprises a process for producing 2-carboxyalkyl(aryl)phosphinic acid, wherein aryl is phenyl or $C_1$–$C_4$ alkyl substituted phenyl, comprising adding water to a first reaction mixture comprising the products of the reaction of dihalogenated (aryl)phosphine and a carboxylic acid selected from acrylic acid or methacrylic acid, and hydrolyzing said reaction products to produce a second reaction mixture comprising a corresponding 2-carboxyalkyl(aryl)phosphinic acid; wherein water is added at a controlled rate to said first reaction mixture and the temperature is controlled to maintain the reactor contents in a stirrable state, and wherein the temperature is at least about 125° C. before the end of the hydrolysis reaction.

This invention also comprises a process for producing 2-carboxyalkyl(aryl)phosphinic acid, wherein aryl is phenyl or $C_1$–$C_4$ alkyl substituted phenyl, comprising adding water to a first reaction mixture comprising the products of the reaction of dihalogenated (aryl)phosphine and a carboxylic acid selected from acrylic acid or methacrylic acid, and hydrolyzing said reaction products to produce a second reaction mixture comprising 2-carboxyalkyl(aryl) phosphinic acid, and simultaneously removing at least a portion of the hydrogen halide present during the hydrolysis reaction, wherein water is added at a controlled rate to said first reaction mixture to enable removal of at least about 35% of the theoretically available halogen in said first reaction mixture during the hydrolysis, and wherein the temperature at the end of th e hydrolysis reaction is at least 125° C.

In an embodiment of these processes, the temperature after addition of two moles water per mole dihalogenated (aryl)phosphine charged to the reaction between dihalogenated (aryl)phosphine and carboxylic acid is at least 125° C.

This invention also comprises a process for producing 2-carboxyalkyl(aryl)phosphinic acid cyclic anhydride(s) comprising adding water to a first reaction mixture comprising the products of the reaction of dihalogenated (aryl) phosphine, wherein aryl is phenyl or $C_1$–$C_4$ alkyl substituted phenyl, and a carboxylic acid selected from acrylic acid or methacrylic acid, and hydrolyzing said reaction products to produce a second reaction mixture comprising a corresponding 2-carboxyalkyl(aryl)phosphinic acid cyclic anhydride; wherein up to about one mole water per mole of dihalogenated (aryl)phosphine is added at a controlled rate to said first reaction mixture and the temperature is controlled to maintain the reactor contents in a stirrable state, and wherein the temperature after addition of water is at least 75° C.

As with an above described process for producing the 2-carboxyalkyl(aryl)phosphinic acid, the reaction producing 2-carboxyalkyl(aryl)phosphinic acid cyclic anhydride comprises simultaneously removing at least a portion of available hydrogen halide during the hydrolysis reaction. The controlled addition of one mole water or less per mole of dihalogenated (aryl)phosphine charged to the reaction enables the removal of at least about 35% of the theoretically available halogen in said first reaction mixture during the hydrolysis.

The corresponding cyclic anhydride, besides being an important intermediate in the process of the instant invention to produce 2-carboxyalkyl(aryl)phosphinic acid, has other uses such as replacing 2-carboxyalkyl(aryl)phospinic acid, as a reactant in chemical reactions (due to the higher reactivity of the cyclic anhydride).

BRIEF DESCRIPTION OF THE DRAWINGS

FIG. 1 is a plot of the mother liquor filtration rate data of the product of this invention at 14 psig filtration pressure and the mother liquor filtration rate of the 16.5:1 control run at 14 psig filtration pressure.

FIG. 2 is a plot of the wash liquor filtration rate data of the product of this invention at 14 psig filtration pressure and wash liquor filtration rate of the 16.5:1 control run at 14 psig filtration pressure.

FIG. 3 is a plot of the mother liquor filtration rate data of the product of this invention at 5 psig filtration pressure and the mother liquor filtration rate of the 16.5:1 control run at 5 psig filtration pressure.

FIG. 4 is a plot of the wash liquor filtration rate data of the product of this invention at 5 psig filtration pressure and the wash liquor filtration rate of the 16.5:1 control run at 5 psig filtration pressure.

FIG. 5 is a comparison of the invention with the 16.5:1 control and displays the concentration of chloride in dry 2-carboxyethyl(phenyl)phosphinic acid.

FIG. 6 is a comparison of the invention with the 16.5:1 control and displays the color of dry 2-carboxyalkyl(phenyl) phosphinic acid.

FIG. 7 is a comparison of the invention with the 16.5:1 control and displays the concentration of benzene phosphonic acid in dry 2-carboxyalkyl(phenyl)phosphinic acid.

DETAILED DESCRIPTION OF THE INVENTION

Figure 1:
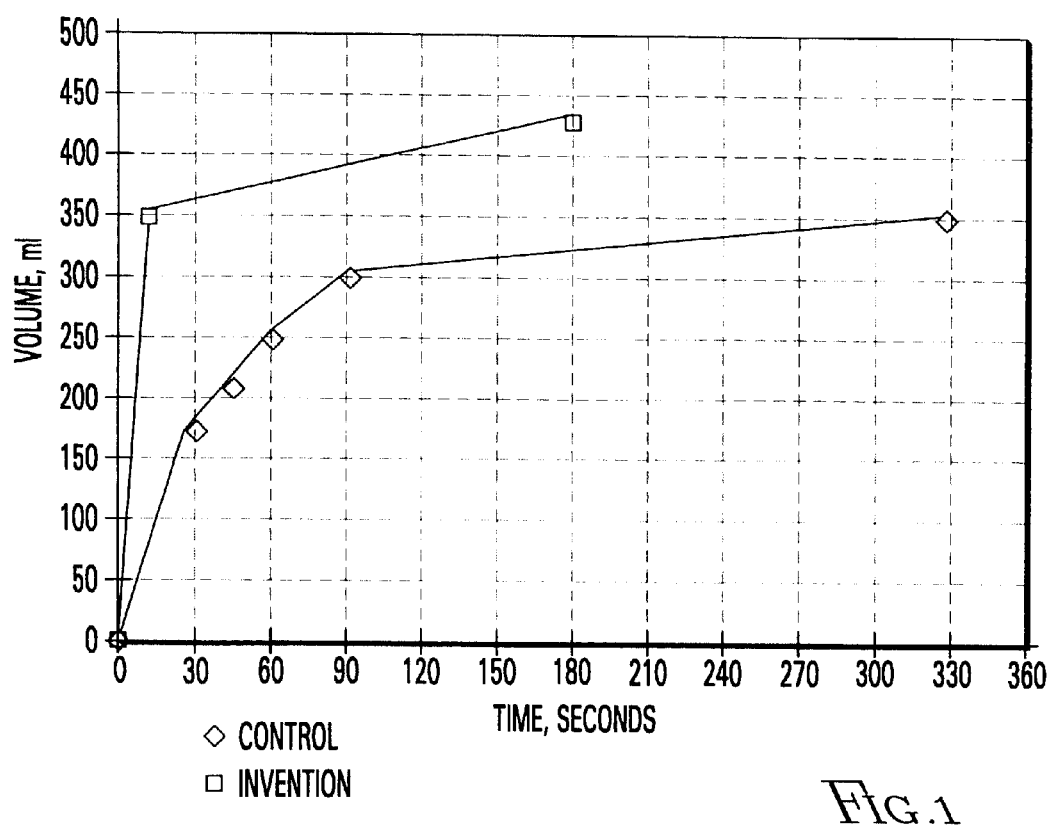
FIGS. 1, 2, 3 and 4 show filtration rate data obtained from Examples 2–3 hereinafter following.

As employed herein, the term "aryl" means phenyl and $C_1$–$C_4$ alkyl substituted phenyl. As employed hereinafter, the term "dichloro" includes dichloro, dibromo and mixtures thereof. Also as used herein, the term "dihalogenated" means "dihalo" and vice versa.

The 2-carboxyalkyl(aryl)phosphinic acid prepared according to the process of this invention depends on the carboxylic acid and aryl employed. Illustratively, when acrylic acid is employed and aryl is phenyl, the 2-carboxyethyl(phenyl)phosphinic acid is 2-carboxyethyl (phenyl)phosphinic acid (I) also known as 3-(hydroxyphenyl-phosphinyl)propanoic acid or 3-HPP shown in (I) below.

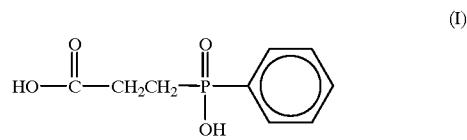

(I)

Illustratively, when methacrylic acid is employed, the 2-carboxyalkyl(phenyl)phosphinic acid is 2-carboxypropyl (phenyl)phosphinic acid (II), also known as 3-(hydroxyphenyl-phosphinyl)-2-methylpropanoic acid).

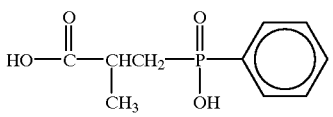

(II)

The preferred carboxylic acid is acrylic acid and the preferred 2-carboxyalkyl(aryl)phosphinic acid is 2-carboxyethyl(phenyl)phosphinic acid. A preferred alkyl substituted aryl is a methyl ($C_1$) substituted phenyl.

Illustratively, the reaction of dichlorinated(phenyl) phosphine, known also as benzene phosphorus dichloride (BPD), with a carboxylic acid (preferably an unsaturated carboxylic or vinylic carboxylic acid) to produce a first reaction acrylation) mixture can be carried out with stoichiometric amounts of the two immediately aforementioned reactants or with a molar excess of carboxylic acid typically up to about 45% molar excess. For example, when acrylic acid is employed as the carboxylic acid, a molar excess of acrylic acid can be used such as disclosed in the '463 patent and the '182 patent. It is currently preferred to conduct this acrylation reaction in the presence of about 10–20% molar excess of carboxylic acid.

When acrylic acid is employed, the first reaction mixture (i.e., acrylation intermediate) comprises one or more compounds selected from 3-(chlorophenylphosphinyl)propionyl chloride, the cyclic anhydride of 2-carboxyethyl(phenyl) phosphinic acid, and the mixed anhydride of acrylic acid with 3-chlorocarbonylethyl(phenyl)phosphinic acid, as disclosed in the '463 patent. The first reaction mixture may also contain minor amounts of other derivatives of acrylic acid including, but not limited to, 3-chloropropionic acid which is formed by the reaction of acrylic acid with HCl.

When methacrylic acid is used, the first reaction mixture (i.e., acrylation intermediate) comprises one or more compounds selected from 3-(chlorophenylphosphinyl)-2-methylpropionyl chloride, the cyclic anhydride of 2-carboxypropyl(phenyl)phosphinic acid, and the mixed anhydride of methacrylic acid with 3-chlorocarbonyl-2-methylethyl(phenyl)phosphinic acid. The first reaction mixture may also contain minor amounts of other derivatives of methacrylic acid including, but not limited to, 3-chloro-2-methylpropionic acid which is formed by the reaction of methacrylic acid with HCl.

Various dihalogenated (aryl)phosphines are commercially available or if desired may be prepared by Friedel-Crafts alkylation of appropriate aromatic compound(s) using $PX_3$, wherein X is selected from chlorine or bromine.

When the hydrolysis reaction is conducted using the water levels of the instant invention, available HCl (or HBr) generated during the hydrolysis reaction or present in the first reaction mixture can be removed from the second reaction mixture as hydrolysis proceeds. The amount of HCl capable of being removed will be dependent on the amount of water added to the first reaction mixture for conducting the hydrolysis. Preferably, all of the HCl capable of being removed is removed during the hydrolysis reaction of this invention. In addition, some 3-chloropropionic acid or 3-chloro-2-methyl propionic acid (depending on the specific carboxylic acid used) may also be removed with the HCl during hydrolysis. Hereinafter the term "HCl" is employed to denote hydrogen chloride or hydrogen bromide as respectfully available halogen depending, of course, on the choice of dihalogenated reactant. Those of skill in the art will recognize that HBr can be produced in situations where HCl is illustrated.

In connection with the several embodiments of this invention, the amount of water admixed with the first reaction mixture in the acrylation step is the amount effective to enable removal of at least about 35%, preferably at least about 60%, and more preferably at least about 85%, of the theoretically available chlorine in said first reaction mixture during hydrolysis.

During the hydrolysis reaction of the embodiments of the invention, it is preferred that substantially all of the HCl available for removal is removed from the reaction vessel used for conducting the hydrolysis reaction. The HCl removed can be recovered for further use or sale.

The temperature employed in the hydrolysis reaction of the process of this invention depends on the amount of water added to the first reaction mixture, i.e. amount of water present during hydrolysis. Generally, the lower the quantity of water added to the reaction mixture, the higher the hydrolysis temperature. Typically, the hydrolysis temperature will be about 60° C.–150° C., preferably about 85° C.–130° C.

The hydrolysis reaction can be conducted under suitable pressures ranging from vacuum to greater than atmospheric pressure if desired. It is preferred to conduct the hydrolysis reaction at or near atmospheric pressure due to excellent results obtained under those operating conditions.

Further according to the process of this invention, preferably once the hydrolysis reaction has been completed, additional water is added to the second reaction mixture to produce a diluted second reaction mixture. During addition of the additional water, the temperature of the reactor contents are preferably maintained above the crystallization temperature.

The crystallization of the 2-carboxyalkyl(phenyl) phosphinic acid can be conducted using conventional crystallization techniques. Typically, the temperature of the diluted second reaction mixture is cooled slowly, e.g. at 0.2° C. per minute, until crystallization is approximately 90% complete. At that point, the cooling rate can be increased if desired and the diluted second reaction mixture further cooled to a suitable temperature at which recovery of 2-carboxyalkyl(phenyl)phosphinic acid can be carried out.

Following crystallization, the 2-carboxyalkyl(phenyl) phosphinic acid can be recovered by filtration or other conventional solids separation techniques. The solids may be then washed and dried. The mother liquor or wash liquors obtained during filtration and washing can be recycled for use in a subsequent hydrolysis step in order to minimize waste.

Several benefits are provided by the practice of the process of this invention. The process of the invention produces 2-carboxyalkyl(phenyl)phosphinic acid having improved filterability over the prior art where hydrolysis is conducted with higher levels of water and crystallization is conducted with higher levels of HCl and 3-chloropropionic acid or 3-chloro-2-methylpropionic acid in the crystallization liquors. The improved filterability of the process of this invention is advantageous in that it results in more efficient product washing and faster filtration. The removal of hydrogen chloride such as HCl according to the processes of the invention reduces the waste disposal costs and the recovered 2-carboxyalkyl(phenyl)phosphinic acid has higher purity, e.g. lower chloride content in the final product. Removal of the hydrogen chloride such as HCl, produced during the process of this invention has an added advantage in that it may provide for use of less expensive yet suitable alloys in the metallurgy of chemical processing equipment used in the filtration and drying operations.

EXAMPLES

Examples are provided by way of illustration and are not intended to limit the process of this invention in any way.

Example 1

Preparation of Acrylation Intermediate

Charge to Reactor:

286.4 grams (1.6 moles) Benzene Phosphorus Dichloride ("BPD")

132.6 grams (1.84 moles) Acrylic Acid (15 mole % excess)

A 500 ml 4-necked glass reactor equipped with a stirrer, thermocouple, condenser and addition funnel was charged with BPD under a slight nitrogen sweep which was maintained throughout the reaction. The reactor was heated to 65–70° C.

The acrylic acid was charged to the addition funnel. Approximately 5 wt. % of the acrylic acid was added rapidly to the BPD at 65–70° C. The addition was stopped and the reaction mass was held for 10–15 minutes during which time a temperature rise was noted. At the end of the hold period said acrylic acid addition was continued at a rate to complete the addition in 0.5–2.0 hours while maintaining a temperature of 60–80° C. in the reaction. The reaction mixture was exothermic.

At the end of the addition, the reaction mass was held for approximately 0.25 hour at 65–80° C. The reaction mass was then heated to 125–130° C. over a period of 1–2 hours and finally held at 125–130° C. for 0.25–1.0 hour.

The conversion of BPD to acrylation intermediate was determined by using phosphorus nuclear magnetic resonance ("NMR") or ion chromatography on the acrylation intermediate composition. The reaction was considered complete when little or no BPD (less than 0.3% of initial charge) was observed in the phosphorus NMR.

When the reaction was deemed to have reached completion, the reactor was cooled to 20–25° C. and was held for the next process step.

The yield was approximately 419 grams of acrylation intermediate.

Although this reaction can be run at temperatures up to 150° C., it has been found that lower temperatures in the initial stages of the reaction process of this invention lead to an improved color in the intermediate which leads to improved color in the final product. Experiments have shown that a temperature increase to 100° C. or greater in the early stages of this reaction will produce a more colored product even if the overall temperature has been kept low.

The acrylation intermediate prepared herein was retained. The process described in Example 1 above was repeated in several runs to provide additional acrylation intermediate for use in Examples 3, 4 and 5 hereinafter following. More specifically, this acrylation intermediate was subsequently employed to produce 2-carboxyethyl(phenyl)phosphinic acid by this process of this invention, the corresponding acid of the 16.5:1 control and the 2-carboxyethyl(phenyl) phosphinic acid cyclic anhydride by the process of this invention.

Example 2

16.5:1 Control—Preparation of 2-Carboxyalkyl (phenyl)phosphinic acid Using Acrylation Intermediate of Example 1

Deionized water, 476 grams (26.4 moles), was charged to a reactor purged with a continuous flow of nitrogen and the off gases collected. At ambient temperature, addition of 419 grams of acrylation intermediate from an acrylation step similar to that of Example 1. The ratio of moles of water added per mole of dichlorophenyl-phosphine charged to prepare the 419 grams of acrylation intermediate used was 16.5:1. The exothermic nature of the reaction raised the temperature to 85–90° C. as the addition proceeded. Some solids appeared during the reaction which dissolved as the temperature increased. When the addition was completed, the reaction temperature was raised to 90–95° C. and 4–6 grams of 30% hydrogen peroxide were added to destroy any $P_4$ which may have been present as a contaminant from the original dichlorophenylphosphine. The batch was maintained briefly at 90–95° C. and then cooled to 76° C. where seed crystals were added. After 10–15 minutes (to allow crystallization to occur), cooling was resumed until a temperature of 5° C. was reached. The slurry was held at this temperature for 15–30 minutes and then solid 2-carboxyethyl(phenyl)phosphinic acid was filtered off and washed with a total of 476 grams of cold deionized water (according to methods described in 3(b) and 3(c) hereinafter following). The wet cake was dried and a yield of 323.8 grams of 2-carboxyethyl(phenyl)phosphinic acid or about 94.3% was obtained. Essentially no hydrogen chloride was evolved. The bulk density of the dried solid was analyzed and was about 0.504 g/cc.

Example 3

(a) Hydrolysis of Acrylation Intermediate by the Process of this Invention

Charge:

419 grams Acrylation Intermediate prepared following the process of Example 1

476 grams (26.44 moles) deionized water or wash liquor from a previous hydrolysis reaction (sufficient water for both the Hydrolysis and Crystallization steps) 0.2–2.0 grams 30% $H_2O_2$.

A 1-liter 4-necked glass reactor equipped with a stirrer, thermocouple, condenser, addition funnel, and inerted with nitrogen was charged with 419 grams of acrylation intermediate and the stirrer started. The reaction mass was heated to 125–130° C. under a slight nitrogen flow. The 476 grams of deionized water (or recycled wash liquor from a previous hydrolysis reaction) was added drop-wise through the addition funnel. The addition time was 1.0–1.5 hours for the first 12 wt. % (57.6 grams, 3.2 moles as pure water). The reaction was vigorous with a large amount of HCl gas evolved; the majority coming off during the addition of the first 6 wt. % of the water addition. The temperature was maintained at 125–130° C. during this part of the addition. When the next 6 wt. % of the water charge was added, the reaction became very exothermic and the temperature was controlled from about 125–130° C. The water addition was stopped and the reaction mixture was held at 0.1–0.5 hour at 125–130° C. If held too long the reaction mixture would become increasingly solid or increasingly difficult to stir as more HCl was evolved.

At the end of the desired hold period, the water addition was resumed at an increased rate to add the remaining water over about 0.5–1 hour. Once the total water added approached about 25 wt. % of the total charge, the water began to reflux and the reaction vessel temperature decreased to 100–105° C. When the total water addition was complete, the reaction was held at 95–100° C. for 0.5 hour.

The results of multiple experiments determined that during this hydrolysis reaction 95–100 grams of hydrogen chloride was evolved.

When the hold period was complete, 30% $H_2O_2$ was added (about 0.2 to about 2 grams, depending upon the quality of the BPD used in Example 1) until a positive peroxide test using potassium iodide—starch indicator paper was achieved.

The hydrolysis reaction was exothermic and the gas evolution offset this. The temperature at which the water addition begins can be as low as about 60° C., but heating should continue to 125–130° C. The temperature should be about 125–130° C. prior to reaching the end of the addition of the first 12 wt. % of the water (i.e., the first two molar equivalents). This is because the reaction mass contains mostly crude acid at this point and can solidify. If the mass does solidify, increased temperatures will quickly remelt the mass. Solids have appeared at 120–125° C. in some reactions although the mass did not completely solidify at these temperatures.

HCl gas evolution began immediately upon the commencement of water or wash liquor addition. Heating was applied to counter the cooling effect so as to maintain temperature.

The resulting aqueous solution has more HCl removed than other processes. The remaining chloride appeared to be almost completely tied up in chloropropionic acid and little free HCl remained in the reaction mixture. The weight of HCl off gas collected was approximately 88–90 wt. % of the theorized amount present from the original BPD charge.

Example 3(b)

Crystallization and Separation (Washing and Filtration)

The aqueous solution from Example 3(a) immediately above, containing 2-carboxyethyl(phenyl)phosphinic acid was cooled to about 77° C. and seeded with PHOSGARD® PF100 (available from Solutia Inc., 575 Maryville Centre Drive, St. Louis, Mo. 63141, USA), which is Solutia Inc.'s registered trademark for 2-carboxyethyl(phenyl)phosphinic acid sold by Solutia Inc. After seeding, the batch was held at approximately 77° C. for 10–15 minutes, and then cooled slowly at a rate of approximately 0.2° C. a minute to approximately 5° C. The resulting cold slurry of unfiltered crystals contained approximately 38 wt. % final product.

The cold slurry was filtered to produce mother liquor and wet product. The wet product was then washed with 476 grams (26.44 moles) of additional fresh cold (at a temperature less than 10° C.) deionized water to produce a washed product. The mother liquor and wash liquor were recovered and kept separate to allow for possible recycling in a subsequent hydrolysis reaction.

Example 3(c)

Filtration and Washing

Regarding the filtration noted immediately above, the filtration procedure used an 0.002 m² Rosenmund Pocket Filter (Rosenmund Inc, 9110 Forsyth Park Drive, Charlotte, N.C., 28273, USA), made of Hastelloy C, volume 1000 ml, length 680 mm and diameter 50 mm. The filter medium was a 40 micron polypropylene cloth.

Figure 3:
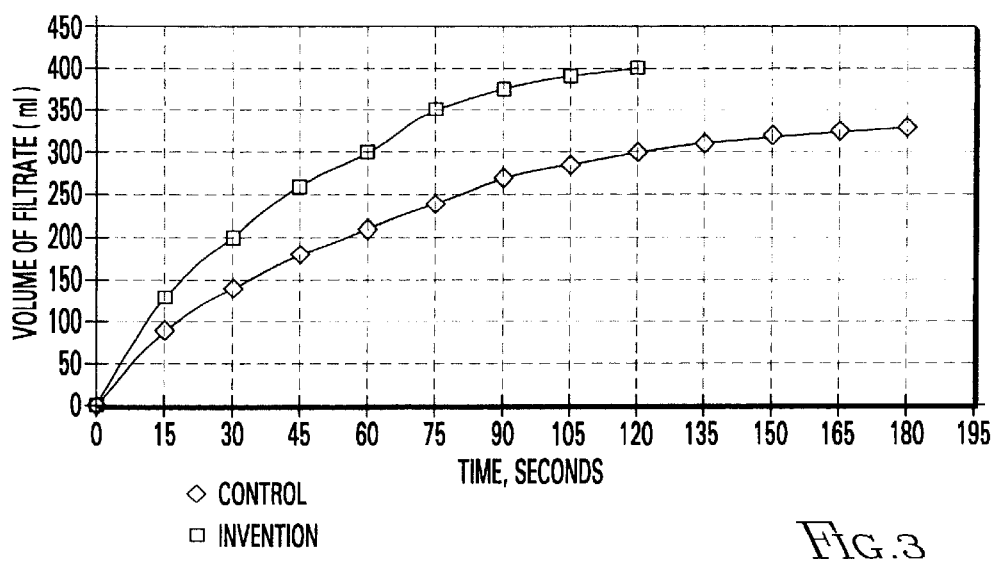

The pocket filter was assembled and pressurized with nitrogen to check for leaks. The top was removed and the cold slurry from the crystallizer was added from the top and the unit pressurized with nitrogen to either 14 or 5 psig. When filtration began, the amount of filtrate versus time was recorded. The pressure was kept constant throughout the test. The data of the mother liquor filtrations are found in FIG. 1 (at 14 psig) and FIG. 3 (at 5 psig).

Figure 2:
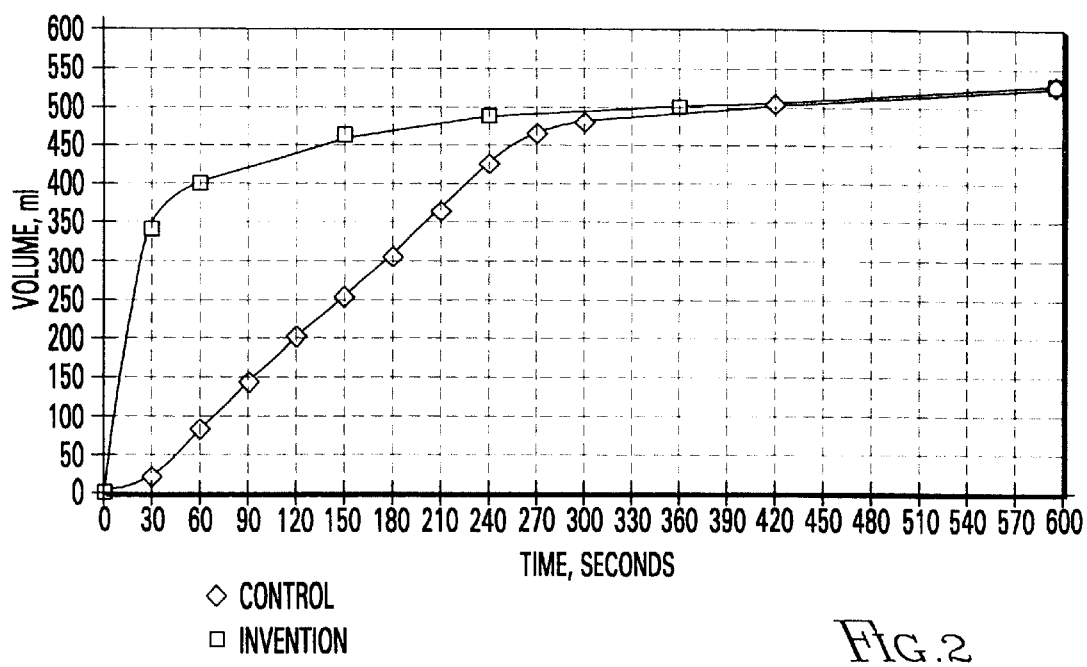
Figure 4:
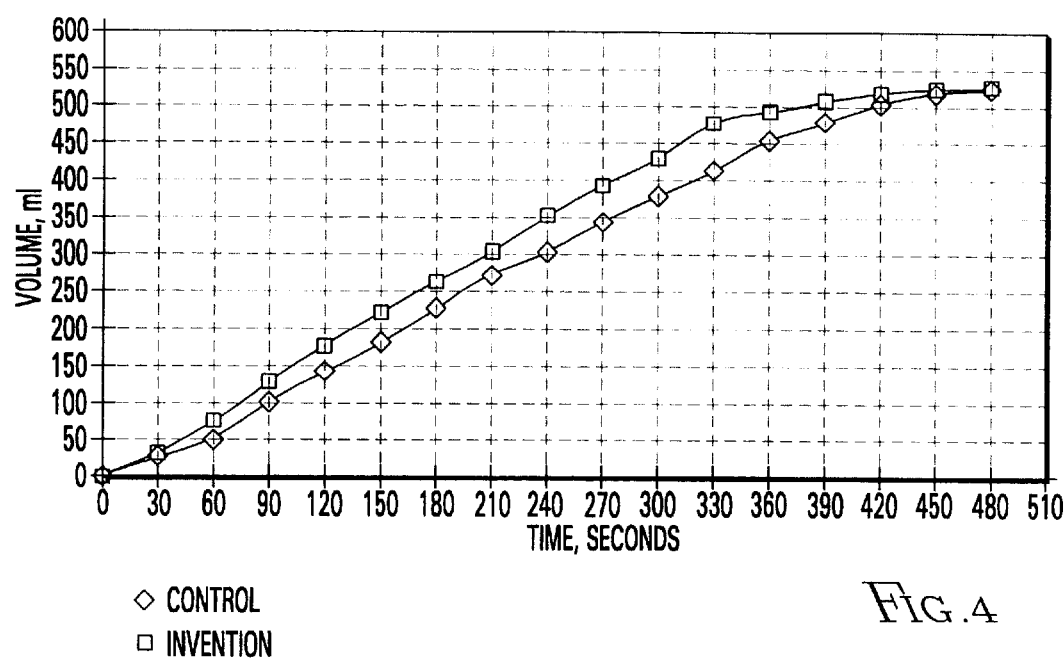

After the cakes for both the 16.5:1 control and for the process of this invention were considered dewatered, the top of the filter was removed and 476 grams cold (at a temperature of less than about 10° C.) water was added from the top for displacement washing. A portion of this wash water was used to rinse traces of the slurry from the crystallizer into the filter at this time. The top of the filter was replaced and the unit pressurized with nitrogen to either 14 psig or 5 psig. When filtration began, the amount of filtrate versus time was recorded. The pressure was kept constant throughout the test. When filtration was complete, the unit was disassembled, the height of the cake in the filter was measured, and the wet filter cake removed. The filter was cleaned and prepared for the next filtration. The data of the wash liquor filtrations are found in FIG. 2 (at 14 psig) and FIG. 4 (at 5 psig).

Tables 1–4 (following) and corresponding attached FIGS. 1–4 provide data collected from the above-described filtration tests.

Table 1 (and FIG. 1) displays mother liquor filtration rates at 14 psig for the process of this invention compared to the mother liquor filtration rates of the 16.5:1 control process. Table 1 (and FIG. 1) demonstrates that the mother liquor filtration rate at 14 psig was substantially better for the invention slurry than for the 16.5:1 control slurry sample.

TABLE 1

|  | Volume Filtrate (ml.) | |
| --- | --- | --- |
| Time (Seconds) | 16.5:1 Control | Invention |
| 0 | 0 | 0 |
| 15 | DNT | 350 |
| 30 | 175 | DNT |
| 45 | 210 | DNT |
| 60 | 250 | DNT |
| 90 | 300 | DNT |
| 180 | DNT | 430 |
| 330 | 350 | DNT |

DNT = Data Not Taken

Table 2 (and FIG. 2) displays wash liquor filtration rates at 14 psig for the process of this invention compared to the wash liquor filtration rates of the 16.5:1 control process. Table 2 (and FIG. 2) demonstrates that the wash liquor filtration rate at 14 psig for the process of this invention was substantially better than the wash liquor filter rate for the 16.5:1 control filter cake.

TABLE 2

|  | Volume Filtrate (ml.) Wash at 5 psig Pressure | |
| --- | --- | --- |
| Time (Seconds) | 16.5:1 Control | Invention |
| 0 | 0 | 0 |
| 30 | 20 | 340 |
| 60 | 80 | 400 |
| 90 | 140 | DNT |
| 120 | 200 | DNT |
| 150 | 250 | 460 |
| 180 | 300 | DNT |
| 210 | 360 | DNT |
| 240 | 420 | 485 |
| 270 | 460 | DNT |
| 300 | 475 | DNT |

TABLE 2-continued

| | Volume Filtrate (ml.) Wash at 5 psig Pressure | |
|---|---|---|
| Time (Seconds) | 16.5:1 Control | Invention |
| 360 | DNT | 500 |
| 420 | 500 | DNT |
| 600 | 525 | 525 |

DNT = Data Not Taken

Table 3 (and FIG. 3) displays mother liquor filtration rates at 5 psig for the process of this invention compared to that of the 16.5:1 control process. Table 3 (and FIG. 3) demonstrates that the mother liquor filtration rate at 5 psig for the slurry of the process of this invention was substantially higher for the 2-carboxyalkyl(phenyl)phosphinic acid produced by the process of this invention than that produced by the 16.5:1 control process.

TABLE 3

| | Volume Filtrate (ml.) | |
|---|---|---|
| Time (Seconds) | 16.5:1 Control | Invention |
| 0 | 0 | 0 |
| 15 | 90 | 130 |
| 30 | 140 | 200 |
| 45 | 180 | 260 |
| 60 | 210 | 300 |
| 75 | 240 | 350 |
| 90 | 270 | 375 |
| 105 | 285 | 390 |
| 120 | 300 | 400 |
| 135 | 310 | DNT |
| 150 | 320 | DNT |
| 165 | 325 | DNT |
| 180 | 330 | DNT |

DNT = Data Not Taken

Table 4 (and FIG. 4) displays wash liquor filtration rates at 5 psig for the process of this invention compared to that of the 16.5:1 control process. Table 4 (and FIG. 4) demonstrates that the wash liquor filtration rate at 5 psig was better for the filter cake of the invention than the 16.5:1 control filter cake.

TABLE 4

| | Time Volume Filtrate (ml.) Wash at 5 psig Pressure | |
|---|---|---|
| Time (Seconds) | 16.5:1 Control | Invention |
| 0 | 0 | 0 |
| 30 | 25 | 30 |
| 60 | 50 | 75 |
| 90 | 100 | 125 |
| 120 | 140 | 175 |
| 150 | 180 | 220 |
| 180 | 225 | 260 |
| 210 | 270 | 300 |
| 240 | 300 | 350 |
| 270 | 340 | 390 |
| 300 | 375 | 425 |
| 330 | 410 | 475 |
| 360 | 450 | 490 |
| 390 | 475 | 505 |
| 420 | 500 | 515 |

TABLE 4-continued

| | Time Volume Filtrate (ml.) Wash at 5 psig Pressure | |
|---|---|---|
| Time (Seconds) | 16.5:1 Control | Invention |
| 450 | 515 | 520 |
| 480 | 520 | 525 |

DNT = Data Not Taken

Based on the filtration rate data in above Tables 1–4 (FIGS. 1–4), it is clear that the process of this invention produces 2-carboxyalkyl(phenyl)phosphinic acid having improved filterability and product handling (as evidenced by improved filtration rates).

Example 3(d)

Drying

The washed product from Example 3(c) above was dried at a pressure of 50 mm Hg and a temperature of 90° C. overnight. The final yield was 327 grams (1.53 moles) or approximately 95.5% based on the original BPD charged. The melting point of the dried product was 156–158° C. The bulk density was determined to be 0.633 grams/cc. The higher bulk density of dried acid product produced in this Example is desired as more dense crystals are provided and higher filtration rates are achieved.

The following procedure was used to measure bulk densities. A 100 ml graduated cylinder was cleaned, dried and weighed. The cylinder was filled to the 100 ml level with dried solid. The cylinder was then tapped on a cork pad (to lessen the chance of breakage) a total of ten times. More solid was added to fill back to the 100 ml mark and the cylinder was tapped an additional five times. The volume of the solid was then measured and the cylinder was weighed. The bulk density of the solid was calculated from the net weight of solid and the observed volume.

The washed product was dried using a drying flask attached to a rotary evaporator. The washed product was placed in the flask, attached to the evaporator and the vacuum was introduced. When the approximate desired vacuum had been reached (~50 mm Hg), heating was applied to 60° C. and held for a couple of hours. Heating was then continued to 90° C. and held overnight.

The washed wet product can be air dried but it has been found that the conditions suggested above allow for removal of some additional impurities (e.g. chloride, chloropropionic acid, etc.) that slowly vaporize during drying. Final dryness was determined by a combination of factors including moisture content and the level of impurities in the dry product.

Figure 6:
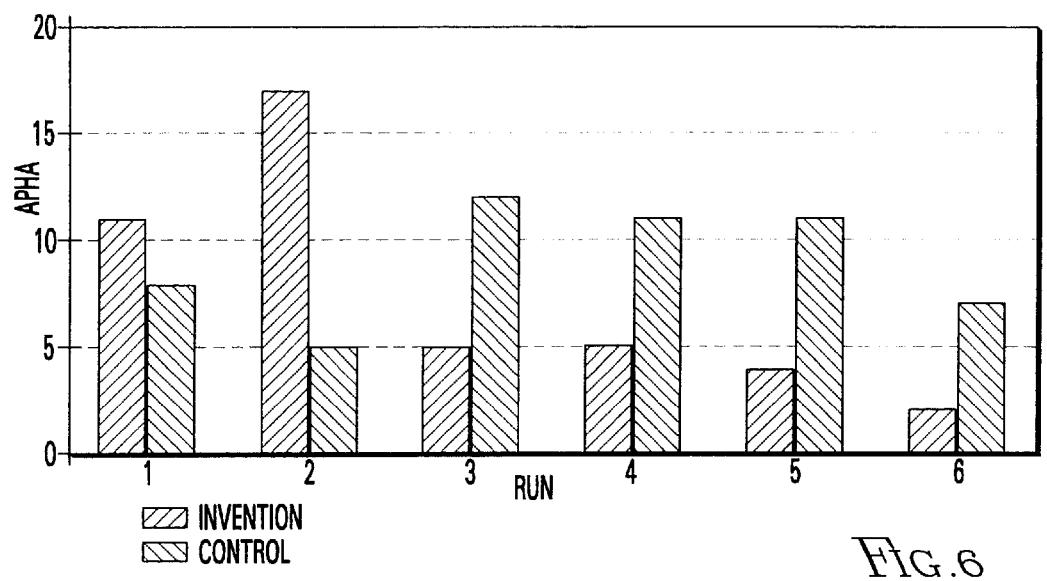
FIG. 6 shows the color of the dry product produced from Examples 1–4.
Figure 7:
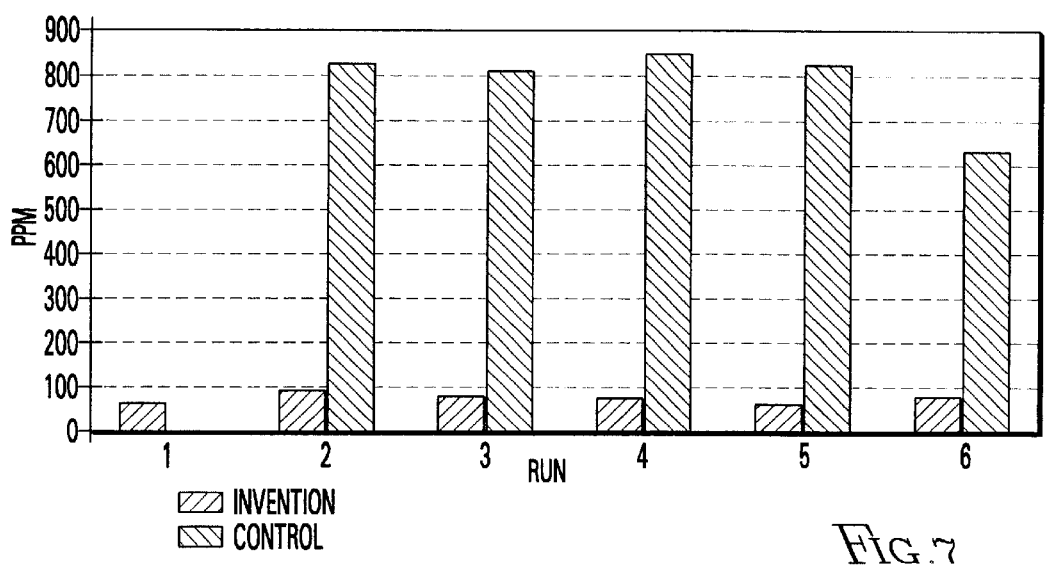

The dry 2-carboxyalkyl(phenyl)phosphinic acid product was then tested for concentrations of chloride, benzene phosphinic acid, chloropropionic acid, color, and benzene phosphonic acid. The results of these tests are displayed in Tables 5–9 (and FIGS. 5–7) for this product as well as the test results on the 2-carboxyalkyl(phenyl)phosphinic acid produced by the 16.5:1 control.

Analysis of dry 2-carboxyalkyl(phenyl)phosphinic acid product acid for chloride, chloropropionic acid, phenylphosphinic acid and phenylphosphonic acid was carried out using the following procedure.

Chloride, chloropropionic acid, benzene phosphinic acid and benzene phosphonic acid are the four major impurities found in 2-carboxyethyl(phenyl)phosphinic acid. The levels of these impurities in the 2-carboxyethyl(phenyl)phosphinic acid produced in the Examples were determined by using an ion chromatographic (IC) method consisting of weighing 1.0000+/−0.1 gram of 2-carboxyethyl(phenyl)phosphinic acid into a 100 ml volumetric flask, diluting to the mark with very low conductivity water, i.e. Milli-Q water, and dissolving the sample. The sample solution was injected into a ThermoSeparation Products SpectraSystem AS3500 IC equipped with a Dionex Ion Pac AS9-HC analytical column and a conductivity detector. The eluent was a gradient mix of Milli-Q water and an aqueous sodium tetraborate solution. The test sample results were compared to a standard stock solution containing the four major impurities and a control sample.

Color Analysis

A color analysis for dry 2-carboxyethyl(phenyl) phosphinic acid was carried out as follows:

Five grams of the dry powder sample were weighed in a beaker. 25 ml of methanol were added. The suspension was stirred to dissolve as much sample as possible. The mixture was transferred to a 30 ml syringe and forced through a 0.45 PVDF or PTFE syringe filter into a 25 ml HACH cuvette. The APHA color is read using Method #8025 (Pt/Co std) in the HACH DR/2000 Direct Reading Spetrophotometer (HACH company, Box 389, Loveland, Colo., USA 80539 relative to a 'blank' cuvette with plain methanol as APHA zero.

Table 5 below displays data which is the concentration of chloride (ppm-wt.) in the final washed and dried 2-carboxyethyl(phenyl)phosphinic acid of this invention as compared to the corresponding acid produced by the process of the 16.5:1 control.

TABLE 5

| | Chloride Concentration in Dry Product - in PPM | |
|---|---|---|
| Run | Invention | Control |
| 1 | 12 | 199 |
| 2 | 15 | 202 |
| 3 | 12 | 206 |
| 4 | 12 | 180 |
| 5 | 16 | 202 |
| 6 | 16 | 206 |

DNT = Data Not Taken

Figure 5:
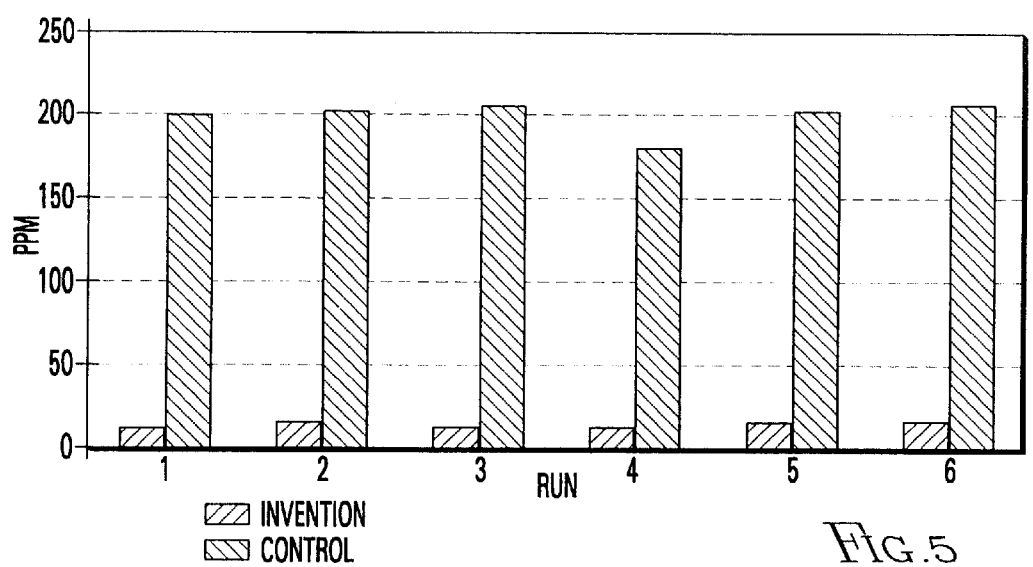
FIGS. 5 and 7 show data concentration of two impurities in the 2-carboxyalkyl (phenyl)phosphinic acid.

FIG. 5 (which depicts the data of Table 5), displays a first run (1) using fresh water, and then run successive runs (2–6) performed with 2-carboxyethyl(phenyl)phosphinic acid product produced utilizing recycled wash liquor retained from a hydrolysis step of the process of this invention. All runs utilized a similarly prepared acrylation intermediate product as prepared by the process (described in Example 1). FIG. 5 shows that the process of the instant invention removes more chloride from the product than the 16.5:1 control process.

Chloride removal is important in the process of this invention to obtain increased crystal size, and to reduce corrosion of equipment used to handle polymers which contain 2-carboxyalkyl(phenyl)phosphinic acid. The removal of the HCl produced during the process of this invention has an added advantage in that it may provide for use of less expensive yet suitable alloys in the metallurgy of chemical processing equipment used in the filtration and drying operations and in polymer operations.

Table 6 displays data of benzene phosphinic acid concentrations in the final product.

TABLE 6

| | Benzene Phosphinic Acid Concentration in Dry Product - in PPM | |
|---|---|---|
| Run | Invention* | Control** |
| 1 | 50 | 25 |
| 2 | 70 | 96 |
| 3 | 50 | 88 |
| 4 | 50 | 100 |
| 5 | 50 | 95 |
| 6 | 50 | 36 |

*Concentration of benzene phosphinic acid is below the detection limit of 50 ppm, except for Run 2 in this table.
**Operated with a detection limit of 25 ppm.

Table 6 shows that the process of the instant invention removes (on average) a greater concentration of benzene phosphinic acid than the 16.5:1 control process. (In these runs, illustrative of this invention, results were not determined below a level of 50 ppm.) Regarding the 2-carboxyethyl(phenyl)phosphinic acid product of this invention, benzene phosphinic acid is regarded as a contaminant which reduces catalyst life useful in downstream applications of 2-carboxyethyl(phenyl)phosphinic acid. Therefore, a lower concentration of benzene phosphinic acid in the final 2-carboxyethyl(phenyl)phosphinic acid product is desired.

Table 7 displays the concentration of chloropropionic acid in the final product. Table 7 shows that the process of this invention removes more chloropropionic acid than the 16.5:1 control process. Removal of chloropropionic acid from the final 2-carboxyethyl(phenyl)phosphinic acid product is desirable. Chloropropionic acid is a contaminant which effects flowability, has an odor, and is a potential chain terminator in polymerization reactions.

TABLE 7

| | Chloropropionic Acid Concentration in Dry Product - in PPM | |
|---|---|---|
| Run | Invention* | Control Process |
| 1 | 50 | 107 |
| 2 | 50 | 209 |
| 3 | 50 | 234 |
| 4 | 50 | 215 |
| 5 | 50 | 174 |
| 6 | 50 | 117 |

Detection Limit: 50 ppm.
*Concentration is below the detection limit of 50 ppm.

Table 8 (and FIG. 6) displays the color of the final 2-carboxyalkyl(phenyl)phosphinic acid product of this invention. A higher number for APHA means a darker color. In Table 8 below, the first run is product from a hydrolysis reaction using fresh water. The subsequent runs for both the process of the invention and for the 16.5:1 control process utilized wash liquor produced in subsequent reactions to perform the hydrolysis reactions.

TABLE 8

Color of Final Product - Measured in APHA

| Run | Invention | Control |
|-----|-----------|---------|
| 1 | 11 | 8 |
| 2 | 17 | 5 |
| 3 | 5 | 12 |
| 4 | 5 | 11 |
| 5 | 4 | 11 |
| 6 | 2 | 7 |

DNT = Data Not Taken

Regarding the data in Table 8 above, color is a factor considered by consumers. A lighter color (lower APHA number) is more desired. The first run and the first recycle show the 16.5:1 control displayed better color than product of the process of the invention. However, the process of this invention had better color in the next four recycle runs than did the 16.5:1 control and suggests improved results for the process of this invention in a commercial operation.

Table 9 (and FIG. 7) displays the concentration of benzene phosphonic acid in the 2-caroxyalkyl(phenyl) phosphinic acid product. This table shows that the process of this invention removes a greater amount of benzene phosphonic acid than does the central process.

TABLE 9

Benzene Phosphonic Acid Concentrate In Dry Product - PPM

| Run | Invention | Control |
|-----|-----------|---------|
| 1 | 62 | DNT |
| 2 | 87 | 822 |
| 3 | 75 | 805 |
| 4 | 70 | 842 |
| 5 | 57 | 818 |
| 6 | 74 | 623 |
| 7 | DNT | 998 |

Example 4

Preparation of 2-Carboxyethyl(phenyl)phosphinic acid Corresponding Cyclic Anhydride Using Acrylation Intermediate from Example 1

Charge to anhydride reactor:
419 grams Acrylation Intermediate
288.8 grams (1.6 moles) fresh deionized water The water charge for producing anhydride was based on the calculated equivalent of BPD charged to the acrylation reaction of Example 1.

A 1-liter 4-necked glass reactor equipped with a stirrer, thermocouple, condenser and addition funnel was charged with 419 grams of acrylation intermediate produced in an acrylation reaction similar to that of Example 1 above and the stirrer was started with a temperature of 90–95° C. The reaction mass was heated to 125–130° C. under a slight nitrogen flow. The 28.8 grams of deionized water was added dropwise through the addition funnel. The addition time was 2–2.5 hours. The reaction was vigorous with a large amount of HCl gas evolved. The temperature was maintained at 125–130° C. during the addition. When the water addition was complete, the reaction was held at 125–130° C. for 0.5 hour.

During this hydrolysis reaction approximately 95–105 grams of hydrogen chloride were evolved.

The hydrolysis reaction was exothermic. The water addition was begun at about 100° C. Heating was continued to a temperature range of 125–130° C. and the temperature was 125–130° C. prior to reaching the end of the addition. Laboratory experiments have shown that although the cyclic anhydride was formed when the reaction was run as low as about 95° C., this lower temperature leads to a less complete reaction with less HCl removal. However, subsequent heating to 125–130° C. provides good conversion.

The HCl gas evolution began immediately upon commencement of the water addition. Beginning the water addition at a slightly lower temperature resulted in a less vigorous gas evolution in the early stages of the addition. Heating was applied to counter the cooling effect and to maintain the temperature.

Much of the remaining chloride appeared to be tied up in the chloropropionic acid with relatively little HCl remaining in the reaction mixture. Traces of chloropropionic acid were present with the HCl in the overhead off-gas and sometimes sublimed into the condenser. The weight of HCl collected overhead was approximately 88–90 wt. % of theory present from the original BPD charge.

Some of the acid form of the anhydride seemed to be present by the end of this reaction. The use of larger amounts of water led to the formation of more of the acid form which was undesirable since the desired product was the cyclic anhydride. The $P^{31}$ NMR of the mixture indicated the presence of two compounds identified as 90–93% cyclic anhydride and 7–10% acid in the mixture at the end of the immediate a foregoing hydrolysis so that the one (1) equivalent charge of water used in this procedure apparently equates to an excess.

Thus, it is apparent that there has been provided, in accordance with the instant invention, a process which satisfies the objects and advantages set forth herein above. While the invention has been described with respect to various examples and embodiments thereof, it is understood that the invention is not limited thereto and many alternatives, modifications and variations will be apparent to those skilled in the art in light of the foregoing description. Accordingly, it is intended to embrace all such alternative, modifications and variations as fall within the spirit and broad scope of this invention.

What is claimed is:

1. A process for producing 2-carboxyalkyl(aryl) phosphinic acid, wherein aryl is phenyl or $C_1$–$C_4$ alkyl substituted phenyl, comprising:
   (a) adding water to a first reaction mixture comprising the products of the reaction of an aryl dihalogenated phosphine selected from aryl dichlorinated phosphine, aryl dibrominated phosphine or a mixture thereof and a carboxylic acid selected from acrylic acid or methacrylic acid, and
   (b) hydrolyzing said reaction products to produce a second reaction mixture comprising said 2-carboxyalkyl (aryl)phosphinic acid;
   wherein said water is added at a controlled rate to said first reaction mixture and the temperature is controlled to maintain the reactor contents in a stirrable state, and wherein the temperature at the end of the hydrolysis reaction is at least 125° C. and hydrogen halide selected from hydrogen chloride, hydrogen bromide or mixtures thereof produced during the hydrolysis reaction is removed.

2. A process for producing 2-carboxyalkyl(aryl) phosphinic acid, wherein aryl is phenyl or $C_1$–$C_4$ alkyl substituted phenyl, comprising:

(a) adding water to a first reaction mixture comprising the products of the reaction of an aryl dihalogenated phosphine selected from aryl dichlorinated phosphine, aryl dibrominated phosphine or a mixture thereof and a carboxylic acid selected from acrylic acid or methacrylic acid, and (b) hydrolyzing said reaction products to produce a second reaction mixture comprising said 2-carboxyalkyl (aryl)phosphinic acid, and simultaneously removing at least a portion of the halide present during the hydrolysis reaction;

wherein said water is added at a controlled rate to said first reaction mixture to enable removal of at least about 35% of the theoretically available chlorine atom or bromine atom in said first reaction mixture during the hydrolysis, and wherein the temperature at the end of the hydrolysis reaction is at least 125° C.

3. The process of claims 1 or 2 wherein the temperature after addition of two moles water per mole of aryl dihalogenated phosphine charged to the reaction between aryl dihalogenated phosphine and said carboxylic acid is at least 125° C. before the end of the hydrolysis reaction.

4. The process of claim 3 wherein said phosphine is dihalo($C_1$–$C_4$ alkyl substituted phenyl)phosphine and said phosphinic acid is 2-carboxyalkyl $C_1$–$C_4$ alkyl substituted phenyl dihalo phosphine acid.

5. The process of claim 3 wherein said phosphine is phenyl dihalogenated phosphine and said phosphinic acid is 2-carboxyalkyl(phenyl)phosphinic acid.

6. The process of claim 3 wherein said temperature of (b) before the end of the hydrolysis reaction is in the range from about 125° C.–170° C.

7. The process of claim 6 wherein said temperature of (b) before the end of the hydrolysis reaction is in the range from about 125° C.–150° C.

8. The process of claim 3 wherein a hydrogen halide selected from hydrogen chloride or hydrogen bromide is removed from said reaction during hydrolysis.

9. The process of claim 6 wherein said phosphine is dichloro(phenyl)phosphine and said phosphinic acid is 2-carboxyalkyl(phenyl)phosphinic acid.

10. The process of claim 1 wherein said dihalo(phenyl) phosphine is dichloro(phenyl)phosphine.

11. The process of claim 1 wherein water is added at a controlled rate to said first reaction mixture to enable removal of at least about 35% of the theoretically available halogen atom in said first reaction mixture during hydrolysis.

12. The process of claim 2 wherein at least about 60% of the theoretically available chlorine atom or bromine atom in said first reaction mixture is removed during the hydrolysis.

13. The process of claim 12 wherein at least about 85% of the theoretically available chlorine atom or bromine atom in said first reaction mixture is removed during the hydrolysis.

14. The process of claim 11 wherein at least about 60% of the theoretically available chlorine atom or bromine atom in said first reaction mixture is removed during the hydrolysis.

15. The process of claim 14, wherein at least about 85% of the theoretically available chlorine atom or bromine atom in said first reaction mixture is removed during the hydrolysis.

* * * * *